United States Patent [19]
Wang et al.

[11] Patent Number: 5,760,048
[45] Date of Patent: Jun. 2, 1998

[54] ALPHA-MERCAPTOACRYLIC ACID DERIVATIVES HAVING CALPAIN INHIBITORY ACTIVITY

[75] Inventors: Kevin Ka-Wang Wang, Ypsilanti; Po-Wai Yuen, Ann Arbor, both of Mich.

[73] Assignee: Warner-Lambert Company, Morris Plains, N.J.

[21] Appl. No.: 635,081

[22] Filed: Apr. 19, 1996

Related U.S. Application Data

[62] Division of Ser. No. 132,624, May 21, 1993, Pat. No. 5,554,767.

[51] Int. Cl.$^6$ ............................................. A61K 31/44
[52] U.S. Cl. ...................... 514/290; 514/510; 514/532; 514/570; 548/440; 560/10; 562/426; 562/427
[58] Field of Search ............................. 514/290, 510, 514/532, 570; 548/440; 560/10; 562/426, 427

[56] References Cited

U.S. PATENT DOCUMENTS

| | | | |
|---|---|---|---|
| 4,124,718 | 11/1978 | Giroux et al. | 424/274 |
| 4,169,149 | 9/1979 | Giroux et al. | 424/274 |
| 4,347,255 | 8/1982 | Giroux et al. | 424/285 |
| 4,439,443 | 3/1984 | Giroux et al. | 424/285 |
| 4,999,436 | 3/1991 | Witzel et al. | 549/45 |
| 5,554,767 | 9/1996 | Wang et al | 548/496 |

FOREIGN PATENT DOCUMENTS

| | | |
|---|---|---|
| 282006A | 4/1983 | Germany . |
| 7193474 | 8/1981 | Japan . |
| 60166641 | 8/1985 | Japan . |
| 7305766 | 2/1975 | South Africa . |

OTHER PUBLICATIONS

T. Murachi, *Biochem Intl*, 1989, 18:263–294.
K. Wang, *TiPS*, 1990, 11:139–142.
B. Meldrum, et al., *TiPS*, Special Report: 1991, 54–92.
R. Siman, et al., *J Neurosci*, 1989, 9:5, 1579–1590.
A. Arai, et al., *Brain Research*, 1990, 532:63–68.
D. Holtzman, et al., *TIBS 16*, 1991, 140–144.
N. Iwamoto, et al., *Brain Research*, 1991, 561:177–180.
R. Siman, et al., *J Neurosci*, 1990, 10:7, 2400–2411.
T.R. Shearer, et al., *Current Eye Research*, 1987, 6:2, 289–300.
J.M. Marcantonio, et al., *Biochemical Society Transactions*, 1991, 19:1148–1150.
M. Azuma, et al., *Current Eye Research*, 1991, 10:7, 657–666.
N.L. Banik, et al., *Central Nervous System Trauma*, 1984, 1:2, 131–137.
W.C. Taft, et al., *Soc Neurosciences Abs*, 1991, 17:65.8.
N. Banik, et al., *J Neurochemistry*, 1985, 45:2, 581–588.
K. Iizuka, et al., *Biochemical Medicine & Metabolic Biology*, 1991, 46:427–431.
G. Toda, et al., *Jpn Heart J*, 1989, 30:3, 375–386.
W. McBride, et al., *New England J of Medicine*, 1988, 318:1734–1737.
K.L. March, et al., *Clinical Research*, 1990, 38:2, 234A.
R.L. Wilensky, et al., *JACC*, 1991, 17:2, 268A.
I. Fukui, et al., *Biochem & Biophy Res Comm*, 1989, 162:2, 559–566.
K. Suzuki, et al., *Biochem J*, 1992, 285:857–862.
H. Sugita, et al., *Calcium Regulation in Biological Systems*, 1984, ed. S. Ebashi, 243–256.
P. Johnson, et al., *Int J Biochem*, 1988, 20:11, 1227–1230.
R.N. Puri, *American J Physiol*, 1990, 259:C862.
J.J. Baldassare, et al., *J Biological Chem*, 1985, 260:19, 10531–10535.
R.N. Puri, et al., *Blood*, 1991, 77:3, 500–507.
B.L. Sharma, et al., *J Applied Tox*, 1986, 6:4, 253–257.
J. Wagner, et al., *Can J Chem*, 1977, 55:4028–4036.
T.H. Haskell, et al., *J Med Chem*, 1970, 13:4, 697–704.

*Primary Examiner*—Joseph McKane
*Assistant Examiner*—Taofiq A. Solola
*Attorney, Agent, or Firm*—Elizabeth M. Anderson

[57] ABSTRACT

The invention covers a novel series of α-mercaptoacrylic acid derivatives that inhibit both calpain I and calpain II with a high affinity and selectivity. The compounds are useful in the treatment of neurodegenerative disorders including cerebrovascular disorders, brain injury, spinal cord, and peripheral nerve injury, cardiac infarction, cataracts, inflammation, restenosis, muscular dystrophy, and platelet aggregation. Pharmaceutical compositions, methods of using processes for preparing and novel intermediates useful in the processes are also disclosed.

18 Claims, 2 Drawing Sheets

ALPHA-MERCAPTOACRYLIC ACID DERIVATIVES HAVING CALPAIN INHIBITORY ACTIVITY

This application is a Divisional application of U.S. Ser. No. 08/132,624, filed May 21, 1993, U.S. Pat. No. 5,554,767.

BACKGROUND OF THE INVENTION

Calcium-dependent protease (calpain) exists in most mammalian cell types. This enzyme has two major isoforms that differ in their sensitivity to calcium ions (calpain I and calpain II) (see Murachi T. *Biochem Int* 1989;18:263–294). Calpain resides in the cytosol of cells and is activated by $Ca^{2+}$ at physiological pH. Its proteolytic activity appears to be selective against certain target proteins, such as components of the cytoskeleton and calmodulin-dependent enzymes. To date, there are no high affinity, selective, nonpeptide inhibitors of calpain reported (see Wang K. K. W., *Trends Pharmacol Sci* 1990;11:139–142).

Excessive excitation by a neurotransmitter glutamate can lead to death of nerve cells (neurons) and neurodegeneration (see Meldrum B., Garthwaite J., *Trends Pharmacol Sci*, Special Report 1991, 1991:54–62. It is believed that toxic effect of glutamate comes from overactivation of its target glutamate receptors (e.g., under ischemic conditions or stroke). This in turn produces an influx of calcium ion ($Ca^{2+}$) into the neurons. The rise of cellular $Ca^{2+}$ level triggers the activation of calpain. Calpain then goes on to degrade cytoskeletal protein such as spectrin, which is believed to disrupt normal cellular functions, and eventually leads to cell death (Siman R., Noszek J. C., Kegerise C., *J Neurosciences* 1989;9:1579–1590). Inhibition of calpain by products covered by the present invention minimizes the cellular damage-and therefore prevents neurodegeneration. Several nonselective calpain inhibitors were shown to be neuroprotective in various ischemia models (Arai A., Kessler M., Lee K. S., Lynch G., *Brain Res* 1990;532:63–68).

Abnormal protein processing is implicated in Alzheimer's disease and calpain and several of its target proteins including the amyloid precursor protein and tau protein have been identified as major components of Alzheimer's neurofibrillary tangles (Holtzman D. M., Mobley W. C., *Trends Biochem Sci* 1991;16:140–144; Iwamoto N. Thangnipon W., Crawford C., Emson P. C., *Brain Res* 1991:177–180) in affected regions of the brain. Amyloid precursor protein has also been found to be sensitive to calpain digestion (Siman R., et al, *J Neuroscience* 1990;10:2400–2411). It is conceivable that calpain activity may be defective that leads to abnormal processing of its target protein. It argues that inhibition of calpain by products covered in the present invention will provide therapeutical benefits to the patients of Alzheimer's disease.

Cataract is an opacity occurring in the lens as a result of a variety of insults to the lens (Shearer T. R., David L. L., Anderson R. S., *Current Eye Res* 1987;6:289–300). In an experimental model where cataract is induced by overdose of sodium selenite (selenite cataract), it has been shown that the lens shows increase of calcium and water-insoluble proteins. Calpain is also found in high concentration in corneal lens epithelium. In selenite cataract, it was demonstrated that lens proteins such as α-, β-crystallins, and cytoskeletal proteins were degraded during cataract formation (Marcantonio J. M., Duncan G., *Biochem Soc Trans* 1991;19:1148–1150). Cysteine protease inhibitor E64, which inhibits calpain, has been shown to reduce the rate of cataract formation in whole animal (Azuma M., David L. L., Shearer T. R., *Current Eye Res* 1991;10:657–666). Calpain inhibitors such as the compounds covered in the present invention can be of use in retarding cataract formation.

It has been demonstrated that intracellular calcium level rises after traumatic injury to brain or spinal cord (Banik N. L., Hogan E. L., Whetstine L. J., Balentine J. D., 1984;1:131–137). Overactivation of calpain is supposed to play a role on the degenerative process that occurs after the injury, similar to the excitatory amino acid toxicity in the brain (Taft W. C., Lyeth B. G., Dixon C. E., Hayes R. L., *Soc Neurosciences* 1991:164, Abstr. 17). There is also evidence of calpain degradation of myelin protein which can cause neurodegeneration (Banik N., McAlhaney W. W., Hogan E. L., *J Neurochemistry* 1985;45:581–588). Calpain inhibitors of the present invention can minimize the degeneration observed.

Ischemic myocardiac infraction is a result of blockade of blood supply in the coronary vessels. It has been reported that calpain activation was observed in the cardiac myocytes during these conditions (Iizuka K., Kawaguchi H., Yasuda H., *Biochemical Medicine and Metabolic Biology* 1991;46:427–431) coronary reperfusion of cysteine protease inhibitor E64c after acute myocardiac infraction in dogs was found to significantly reduce the size of infract (Toda G., Matsushita S., Kuramoto K., et al, *Jap Heart J* 1989;30:375–386). Again, calpain inhibitors in the present invention can provide therapeutic benefits.

Percutaneous transluminal coronary angioplasty is now a widely accepted medical procedure to expand the inner diameter of clotted artery in atherosclerotic coronary artery disease patients. However, the success rate of this procedure is dampened by the spontaneous, slow renarrowing of the arteries (restenosis) (McBride W., Lange R. A., Hillis L. D., *New Eng J Med* 1988;318:1734–1737). Recently, it has been shown that controlling proliferation and migration of smooth muscle cells to the neoinitimal layer of the blood vessel by calpain inhibitor I and other cysteine protease inhibitors (March K. L., Roeske R., Hathaway D. R., *Clin Res* 1990;38:234A). It was further shown that these agents can inhibit restenosis (Wilensky R. L., March K. L., Hathaway D. R., *J Amer Coll Cardiol* 1991;17:268A). Since the compounds in this invention are also calpain inhibitors, they should be useful in reducing angioplastic restenosis.

Calpain is found in the synovial (joint) fluid of the knee joint. In fact, both calpain I and II in the synovial fluid were found to increase by several-fold in rheumatoid arthritis patients (Fukui I., Tanaka K., Murachi T., *Biochem Biophys Res Commun* 1989;162: 559–566). A major cartilage component proteoglycan was also found to be a calpain substrate (Suzuki K., et al, *Biochem J* 1992;285:857–862). It is believed that calpain overactivation has a damaging effect of the joint and in the inflammation process itself. Inhibition of calpain activity by compound in the present instant invention may provide therapeutic benefit to the patients suffering from such inflammation.

Disruption in the regulation of intracellular calcium concentration was reported in muscular dystrophy, such as Duchenne muscular dystrophy (DMD) and after muscle denervation. Intracellular calcium levels in muscular dystrophic mice was found to be significantly raised which resulted in increased protein degradation. Many myofibrillar proteins (such as myosin, Troponin I and T) are indeed good calpain substrates (Sugita H., Ishiura S., Kamakura K., Nakase H., Hagiwara K., Nonaka I., In: *Calcium Regulation in Biological Systems*, (Ebashi S., Endo M., Imahori K., Kakiuchi S., Nishizuka Y., eds. Academic Press, 1984:243–257.) and calpain II concentration was higher in dystrophic skeletal muscle in animals (Johnson P., Hammer J. L., *Int J Biochem* 1988;20:1227–30). Therefore, it is conceivable that calpain overactivation plays an important role in abnormal myofiber degradation. Calpain inhibitors described in this invention will be useful treatment in muscular degenerative disorders such as muscular dystrophy or muscle denervation.

Formation of blood clots (thrombosis) is a result of platelet aggregation. When platelets are stimulated by thrombin or plasmin, two key events occur which lead to platelet aggregation (Puri R. N., et al. *Am J Physiol* 1990;259:C862): 1) putative ADP-receptor aggregin is proteolyzed and 2) fibrinogen receptors become exposed on the platelet surface. Aggregin was hydrolyzed in vitro by calpain but not by thrombin. It was further found that thrombin increased intracellular calcium levels in platelets thus activating calpain which then hydrolyzed aggregin. Calpain also appeared to modify platelet membrane structure thus exposing latent fibrinogen receptor (Baldassare J. J., et al. *J Biol Chem* 1985;260:10531–10535). This allows fibrinogen binding to platelet that leads to aggregation. It was shown that calpain inhibitors Phe-Gln-Val-Val-Cys(3-nitro-2-thiopyridine)-Gly-NH$_2$ and high molecular weight kininogen blocked aggregin breakdown and platelet aggregation (Puri R. N., et al. *Am J Physiol* 1990;259:C862; Puri R. N., et al. *Blood* 1991;77:500–507). Therefore, calpain inhibitors described in this patent should be effective platelet aggregation inhibitors.

SUMMARY OF THE INVENTION

The present invention is a series of α-mercaptoacrylic acids of Formula

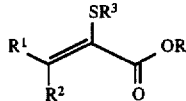

the tautomers or isomers thereof and the pharmaceutically acceptable base or acid addition salt thereof wherein R, R$^1$, R$^2$, and R$^3$ are as described below;

These compounds inhibit both calpain I and calpain II with high affinity and selectivity.

The present invention also includes pharmaceutical compositions comprising therapeutically effective amount of one or more of a compound of Formula I together with a pharmaceutically acceptable carrier in unit dosage form.

The present invention includes methods of using the compounds of Formula I in the treatment of neurodegenerative disorders including cerebrovascular disorders as well as in the treatment of traumatic brain injury, spinal cord and/or peripheral nerve injury, cardiac infraction, cataract, inflammation, restenosis, muscular dystrophy, and platelet aggregation.

The present invention also includes a method of treating disorders responsive to the blockade of one or both of calpain I and calpain II comprising administering to a mammal, including a human, in need thereof a therapeutically effective amount of the above composition.

The invention also includes treating stroke, cerebral ischemia, cerebral infarction, cerebral vasospasm, hypoglycemia, cardiac arrest, Alzheimer's disease, traumatic brain injury, spinal cord and/or peripheral nerve injury, cardiac infraction, cataract, inflammation, restenosis, muscular dystrophy, and platelet aggregation.

The invention further includes processes for the preparation of compounds of Formula I.

The invention still further includes novel intermediates useful in the processes.

BRIEF DESCRIPTION OF THE INVENTION

FIG. I shows increasing concentrations of Example 6 on the horizontal axis and percent of calpain inhibition on the vertical axis.

FIG. II shows treatment with no compound, a reference standard (MK-801) and three compounds of the invention (3, 18, and 22) on the horizontal axis and the amount of NMDA-induced LDH release blocked along the vertical axis.

DETAILED DESCRIPTION OF THE INVENTION

Figure 1:
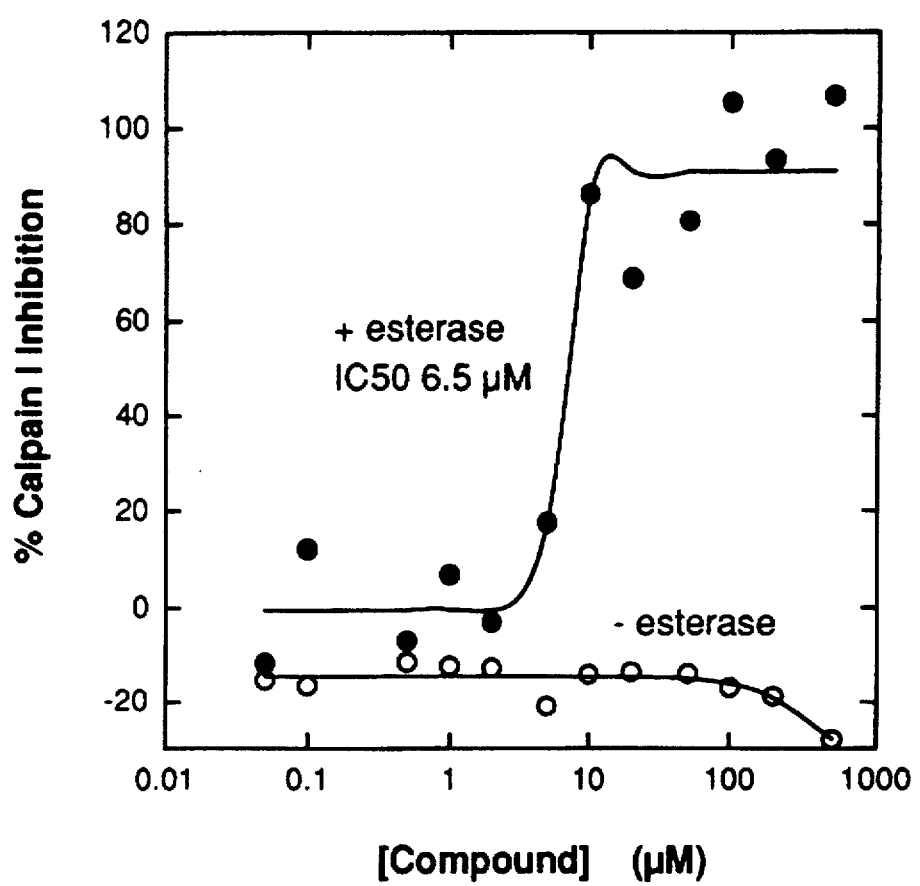
Figure 2:
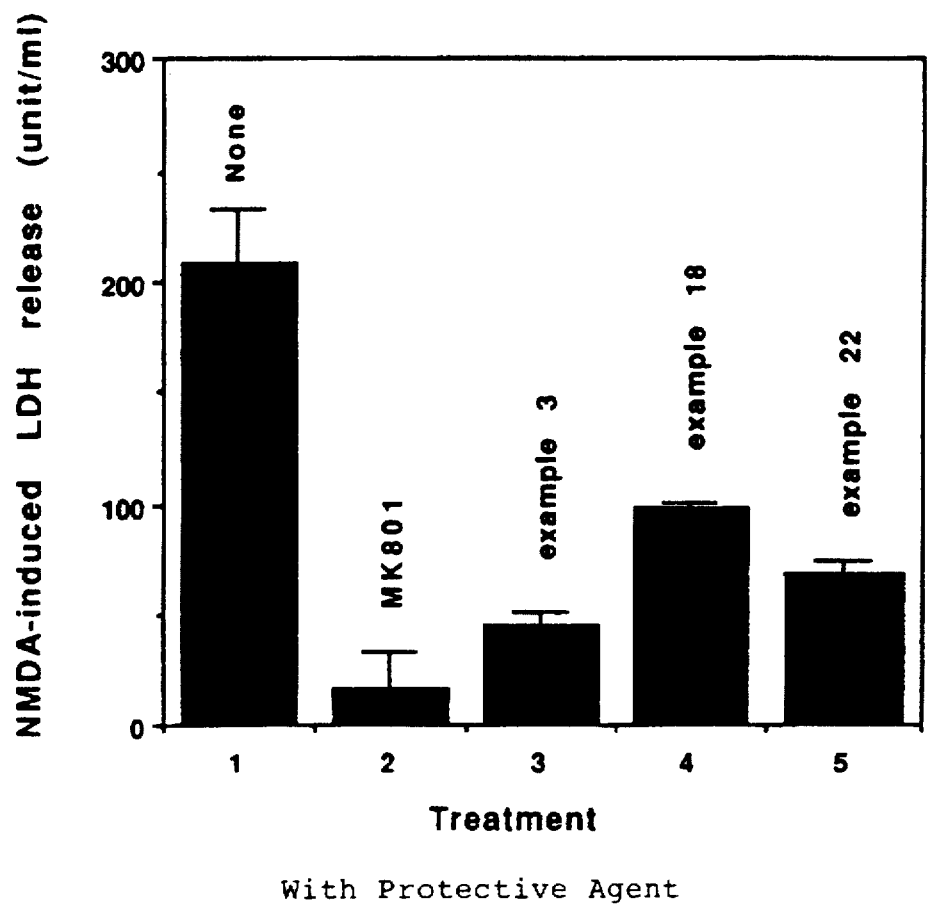

The compounds of the instant invention are the first nonpeptide inhibitors of calpain. These compounds have a novel mechanism of inhibition of the enzyme, at the Ca-binding site.

The α-mercaptoacrylic acid derivatives of the instant invention are those of Formula

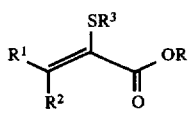

or a pharmaceutically acceptable salt thereof wherein
R is hydrogen,
  alkyl,
  cycloalkyl,
  alkenyl,
  cycloalkenyl,
  alkynyl,
  aminoalkyl,
  aryl, or
  together with R$^3$ forms a ring;
R$^1$ and R$^2$ are each independently hydrogen,
  alkyl,
  cycloalkyl,
  alkenyl,
  cycloalkenyl,
  alkynyl,
  aryl,
  arylalkyl,
  arylalkenyl,
  arylalkynyl,
  heterocycle,
  heterocyclealkyl,
  heterocyclealkenyl,
  heterocyclealkynyl,
when R$^1$ and R$^2$ are each independently hydrogen, alkyl, alkenyl, and alkynyl they can be taken together to form a ring; and
R$^3$ is hydrogen,
  alkyl,
  cycloalkyl,
  alkenyl,
  cycloalkenyl,
  alkynyl,
  aminoalkyl,
  aryl, or
  —COR$^4$ wherein R$^4$ is alkyl, alkenyl, alkynyl, alkoxy, amino, or aryl.

The solvates and hydrates of the above compounds are also part of the instant invention.

Preferred compounds are those of Formula I wherein R is hydrogen or alkyl;

R¹ and R² are each independently hydrogen,
aryl,
heterocycle,
heterocyclealkyl, and R³ is hydrogen
alkyl,
cycloalkyl,
alkenyl,
cycloalkenyl,
alkynyl,
aminoalkyl,
aryl, or
—COR⁴ wherein R⁴ is alkyl, alkenyl, alkynyl, alkoxy, amino, or aryl.

More preferred compounds are those of Formula I wherein

R is hydrogen or alkyl of from one to three carbon atoms;
R¹ is naphthyl,
indole,

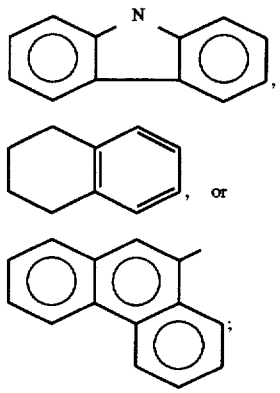

R² is hydrogen; and
R³ is hydrogen.

Still more preferred compounds include but are not limited to:

(a) 3-(2-naphthyl)-2-mercapto-2-propenoic acid;
(b) (Z)-2-propenoic acid, 2-mercapto-3-[4-(phenylmethoxy) phenyl];
(c) 3-(3-indolyl)-2-mercapto-2-propenoic acid;
(d) (Z)-2-propenoic acid, 3-(9-ethyl-9H-carbazol-2-yl)-2-mercapto;
(e) (Z)-2-propenoic acid, 2-mercapto-3-(5,6,7,8-tetrahydro-2-naphthalenyl);
(f) 3-(4-iodophenyl)-2-mercapto-2-propenoic acid;
(g) 3-(4-fluorophenyl)-2-mercapto-2-propenoic acid;
(h) 3-(4-methoxyphenyl)-3-methyl-2-mercapto-2-propenoic acid;
(i) 3-(5-fluoro-3-indolyl)-2-mercapto-2-propenoic acid;
(j) Ethyl-2-naphthyl-2-mercapto-2-propenoate;
(k) (Z)-2-propenoic acid, 3-[1,1'-biphenyl]-4-yl-2-mercapto;
(l) 3-(1-naphthyl)-2-mercapto-2-propenoic acid;
(m) 3-(2-indolyl)-2-mercapto-2-propenoic acid;
(n) 3-(9-phenanthyl)2-mercapto-2-propenoic acid;
(o) (Z)-2-propenoic acid, 2-mercapto-3-(9-phenanthienyl);
(p) (Z)-2-propenoic acid, 3-(2-thienyl)-3-mercapto;
(q) (Z)-2-propenoic acid, 2-mercapto-3-(6-methoxy-2-naphthalenyl;

(r) (Z)-2-propenoic acid, 3-(5-benzodioxoyl)-2-mercapto;
(s) (Z)-2-propenoic acid, 3-(2,5-dimethyl-1-phenyl-1H-pyrrol-3-yl)-2-mercapto;
(t) (Z)-2-propenoic acid, 3-[4-(1,1-dimethylethyl)phenyl]-2-mercapto;
(u) (Z)-2-propenoic acid, 3-[2-(4-chlorophenyl)-1H-indol-3-yl]-2-mercapto;
(v) (Z)-2-propenoic acid, 2-mercapto-3-[4-(2-phenylethl) phenyl];
(w) (Z)-2-propenoic acid, 3-(3-thienyl)-2-mercapto; and
(x) 2-Propenoic acid, 3-(9H-fluoren-2-yl)-2-mercapto.

The alkyl groups contemplated in the instant invention such as alkyl per se, aminoalkyl, arylalkyl, heterocycloalkyl are both straight and branched carbon claims.

Lower alkyl means a straight chained or branched chain of from one to six carbon atoms including but not limited to methyl, ethyl, propyl, n-propyl, butyl, 2-butyl, isobutyl, pentyl, hexyl, n-hexyl, and the like. The alkyl groups may be unsubstituted or substituted by one or more selected from: halogen, hydroxy, amino, and alkoxy.

Alkenyl means a group from two to six carbon atoms, containing at least one double bond. These are, for example, but not limited to ethylene, 1,2- or 2,3-propylene, 1,2-, 2,3-, or 3,4-butylene, 1,2-, 2,3-, 3,4- or 4,5-pentylene, or hexylene, or isomers thereof.

Alkynyl means a group from two to about six carbon atoms, containing at least one triple bond. These are, for example, but not limited to ethynyl, 2,3-propynyl or 3,4-butynyl, or isomers thereof.

Cycloalkyl means a saturated ring of from three to about six or seven carbon atoms. Such groups included but are not limited to cyclopropyl, cyclobutyl, cyclopentyl, cyclohexyl which are unsubstituted or substituted by one or more selected from: halogen, alkoxy, alkyl, or hydroxy.

Cycloalkenyl means an unsaturated ring of from four to six carbon atoms containing one or two carbon-carbon double bond(s).

Heterocycle means a 5- or 6-membered monocyclic, bicyclic, or tricyclic group, containing at least one to as many as four heteroatoms in one ring if monocyclic or at least one of the rings, if fused bicyclic or tricyclic. Heteroatoms are nitrogen, oxygen, or sulfur or a combination thereof, where possible. Such heterocycles include, thienyl, benzothienyl, furanyl, benzofuranyl, pyrazinyl, pyrazolyl, pyridazinyl, pyridyl, pyrimidinyl, pyrrolyl, isothiazolyl, thiazolyl, oxazolyl, isoxazolyl, triazolyl, tetrazolyl, imidazolyl, thiadiazolyl, benzothiadiazolyl, oxadiazolyl, benzothiazolyl, indolyl, carbazolyl, quinolinyl, isoquinolinyl, or N-oxides thereof.

The term aryl includes substituted or unsubstituted phenyl, naphthyl, and biphenyl. The substituents include one or more selected from: halogen, nitro, alkyl, alkoxy, alkylthio, hydroxy, or others as specified.

The term halogen includes fluorine, chlorine, bromine, and iodine.

R and R³ definitions include pharmaceutically acceptable hydrolytically labile groups. Such hydrolytically labile groups are recognized by artisans of ordinary skill to include groups convertible under physiological conditions to a free hydrogen.

Well known protecting groups and their introduction and removal may be used according to the skill in the art and are described, for example, in McOmie J. F. W., *Protective Group in Organic Chemistry*, Plenum Press, London, New York (1973) and Greene T. W., Wuts P. G. M., *Protective Groups in Organic Synthesis*, Second Edition, Wiley, New York (1991).

The compounds of the present invention may contain asymmetric carbon atoms. The instant invention may also include the individual diastereomers and enantiomers, which may be prepared or isolated by methods known to those skilled in the art.

Selected compounds of the present invention can exist also as syn and anti forms and are also claimed in the present invention. Selected compounds can also exist as E and Z double bond isomers. Both forms are included in the present invention.

The compounds of the present invention can also exist in tautomeric forms. Both the thioenol form and the thioketo form are therefore claimed in this invention.

Any resulting racemate can be resolved into the optical antipodes by known methods, for example by separation of the diastereomeric salts thereof, with an optically active amine, and liberating the optically active acid compound by treatment with an acid. Racemic compounds of the present invention can thus be resolved into their optical antipodes e.g., by fractional crystallization of d- or 1-α-methylbenzylamine, brucine, quinidine, or quinine salts.

Additional methods for resolving optical isomers, known to those skilled in the art may be used, for example those discussed by J. Jaques, A. Collet, and S. Wilen in *Enantiomers, Racemates, and Resolutions*, John Wiley and Sons, New York (1981).

Pharmaceutically acceptable salts of the compounds of Formula I are also included as a part of the present invention.

The base salts may be generated from compounds of Formula I with one equivalent of a suitable nontoxic, pharmaceutically acceptable base followed by evaporation of the solvent employed from the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well-known to practitioners of the pharmaceutical formulation arts.

See, for example, Berge S. N., et al, *J Pharm Sci* 1977;66:1–19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well-known in the art.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

The compounds of the present invention can be administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low-melting wax, cocoa butter, and the like. The term "preparation" is intended to include the formulation of the active compound with encapsulating material as a carrier providing a capsule in which the active component, with or without carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low-melting wax, such as a mixture of fat glycerides or cocoa butter, is first melted and the active component is dispersed homogeneously therein, as by stirring. The molten homogeneous mixture is then poured into convenient-sized molds, allowed to cool, and thereby to solidify.

Liquid form preparations include solutions, suspension, and emulsions, for example, water or water propylene glycol solutions. For example, parenteral injection liquid preparations can be formulated in solution, such as, in aqueous polyethylene glycol solution.

Aqueous solutions suitable for oral use can be prepared by dissolving the active component in water and adding suitable colorants, flavors, stabilizing, and thickening agents, as desired.

Aqueous suspensions suitably for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg preferably 10 mg to 100 mg according to the particular application and the potency of the active component. The composition can, if desired, also contain other compatible therapeutic agents.

The compounds of the instant invention exhibit valuable pharmacological properties by selectively inhibiting the calcium-dependent neutral proteases in mammals. The compounds are thus useful for treating diseases responsive to calcium-dependent neutral proteases inhibition in mammals.

Such disorders include but are not limited to cerebral ischemia or cerebral infarction resulting from a range of conditions such as thromboembolic or hemorrhagic stroke, cerebral vasospasm, hypoglycemia, cardiac arrest, status epilepticus, and perinatal asphyxia, anoxia such as from drowning, pulmonary surgery, and cerebral trauma. Other treatments are for neurodegenerative disorders such as Alzheimer's disease, spinal cord and/or peripheral nerve injury, and poisoning by exogenous NMDA poisons (e.g., some forms of lathyrism). Further uses include treatment for cardiac infraction, cataract, inflammation, restenosis, muscular dystrophy, and platelet aggregation.

Specifically, the compounds of the present invention have activity as inhibitors of the calcium-dependent neutral proteases. As such, the compounds of the present invention are calpain-specific cysteine proteinase inhibitors.

For example, compounds of the invention exhibit valuable biological properties because of these calcium-depending neutral proteases inhibiting properties. These properties may be ascertained in one or more of the following assays.

Assay of Calpain Activity

Calpain I was purified from human erythrocytes as described by Wang K. K. W., Roufogalis B. D., Villalobo A., *Arch Biochem Biophys* 1988;267:317–327. Calpain activity was assayed in a 96-well microplate format (Buroker-Kilgore M., Wang K. K. W., *Anal Biochem* 1993;208:387–392). In 250 µL of reaction mixture, substrate casein (0.5 mg/mL) was incubated with 0.01 unit (80–120 ng) calpain I, 20 mM dithiothreitol (DTT), 50 mM Tris-HCl (pH 7.4 at 25° C.), and 4 mM $CaCl_2$ at 25° C. for 60 minutes. Two 100-µL aliquots were taken for Coomassie blue binding analysis to quantify the remaining casein.

As can be seen from the results of Table I below, the thiol-acrylates listed showed various potency against calpain I in this in vitro assay. Compound concentrations that cause 50% inhibition ($IC_{50}$) are as shown. Compound of Example 6 is an ethyl ester pro-drug which shows activity only after it is hydrolyzed by cellular esterase (see below).

TABLE I

| Inhibitory Activity Against Human Calpain I | |
|---|---|
| Example | $IC_{50}$ (µM) |
| 3 | 2.6 µM |
| 4 | 0.45 µM |
| 6 | >500 µM |
| 8 | 0.36 µM |
| 10 | 1.2 µM |
| 12 | 1.1 µM |
| 14 | 66% at 200 µM |
| 16 | 3.0 µM |
| 18 | 1.8 µM |
| 20 | 3.6 µM |
| 22 | 1.3 µM |
| 25 | 1.7 µM |
| 27 | 3.1 µM |
| 29 | 4.0 µM |
| 31 | 3.2 µM |
| 34 | 2.1 µM |
| 36 | 1.2 µM |
| 38 | 13.6 µM |
| 40 | 7.8 µM |

TABLE I-continued

| Inhibitory Activity Against Human Calpain I | |
|---|---|
| Example | $IC_{50}$ (µM) |
| 42 | 6.0 µM |
| 44 | 1.7 µM |
| 47 | 2.7 µM |
| 49 | 7.5 µM |
| 51 | 5.9 µM |
| 53 | 1.6 µM |

Treatment of Compound of Example 6 With Esterase

Various concentrations of the compound of Example 6 (250 nM to 2.5 mM) were pretreated with 0.2 unit rabbit liver esterase (Sigma E9636) in 50 µL containing 50 mM Tris-HCl (pH 7.4 at 25° C.), 5 mM DTT at 25° C. for 60 minutes. The mixture was then tested for calpain inhibition with the calpain assay described above.

As can be seen from the data in FIG. I, as high as 500 µM of the compound did not inhibit calpain I. However, upon preincubation of esterase, the compound showed strong inhibition on calpain. The esterase presumably hydrolyzed the only ester bond in the molecule, producing the free acid compound which is identical to the compound of Example 3.

Casein Breakdown

Casein (15 µM) was incubated with 0.8 nM calpain I, 15 mM DTT, 45 mM Tris-HCl (pH 7.4 at 25° C.) and in the presence or the absence of compound Example 3 (30 µM) for up to 120 minutes. Aliquots of the samples were taken at several time points and subjected to SDS-polyacrylamide gel electrophoresis (SDS-PAGE) as described by Laemmli U. K., *Nature* 1970;331:315–319. Casein and its fragments were visualized by Coomassie G250 staining of the gel.

Analysis of the stained gels showed the intact protein casein (α and β forms as 32, 34 kDa bands) were degraded by calpain I into small molecular weight fragments in 5 to 120 minutes. On the other hand, the presence of 30 µM compound Example 3 almost completely blocked the degradation of casein at all time points. These results confirmed that the thiol-acrylates inhibits calpain-mediated proteolysis of protein substrate.

Selectivity of Thiol-acrylates

Calpain I was assayed as described (α-mercaptoacrylic acid). Ten to 20 ng papain (papaya latex, Sigma, P3125), 1.25 µg trypsin (bovine pancreas, Sigma, T8003), and 5 µg thermolysin (*Bacillus thermoproteolyticus*, Sigma, P1512) were assayed using 0.5 mg/mL casein as substrate in the microplate format (250 µL reaction volume), essentially as described by Buroker-Kilgore M., Wang K. K. W., *Anal Biochem* 1993;208:387–392. Inhibition of these proteases are presented as $IC_{50}$.

As shown in Table II below, examples of thiolacrylate inhibited calpain I with $IC_{50}$ between 0.36 µM to 5.9 µM but did not inhibit trypsin (a serine protease) or papain (a cysteine protease). Metallo-protease thermolysin was inhibited only at very high concentrations. $IC_{50}$s against thermolysin are all greater than 200 µM. Therefore, these results showed that the thiol-acrylates one very selective for calpain over other proteases.

TABLE II

| Inhibitory Activity of Thiol-Acrylates Against Various Proteases | | | | |
|---|---|---|---|---|
| Compound | Calpain | Papain | Trypsin | Thermolysin |
| 3 | 2.4 μM | >200 μM | >200 μM | 394 μM |
| 8 | 0.36 μM | >500 μM | >500 μM | 204 μM |
| 22 | 1.3 μM | >200 μM | >200 μM | 248 μM |
| 51 | 5.9 μM | >200 μM | >200 μM | 367 μM |

Assay of Lactate Dehydrogenase (LDH)

Fetal rat cortical cell cultures were grown on 12-well plates as described by Koh J. Y., Choi D. W., *J Neurosci Methods* 20 1987;20:83–90). Seventeen-day-old cultures were pretreated with 200 μM calpain inhibiting compound (when added) for 1 hour before treatment of 500 μM N-methyl-D-aspartate (NMDA) for 30 minutes (in the absence or the presence of the compound). After an additional 4 hours in the absence or the presence of the compound, LDH release from neurons to the medium as a measurement of NMDA-induced cell death was performed similarly as described by Koh J. Y., Choi D. W., *J Neurosci Methods* 1987;20:83–90.

Data shown in FIG. II illustrated that NMDA induced about 210 unit/mL LDH release from the cells which was blockable by NMDA receptor antagonist MK-801. It also showed that examples of thiol-acrylate Example 3 and 18 partially blocked the NMDA-induced LDH release. These results would suggest that the thiolacrylates described in this patent are neuroprotective.

Spectrin Breakdown Measurement

Rat cortical cell cultures were treated with NMDA in the absence or presence of calpain inhibiting compounds as described in "Assay of LDH" above. At the end of the 4-hour post-NMDA incubation, cells were lysed with 300 μL buffer containing 20 mM Tris-HCL (pH 7.4 at 4° C.), 1% SDS, 5 mM EGTA, 5 mM EDTA, 1 mM DTT, and various protease inhibitors. Total cellular protein was precipitated by 100 μL of 100% trichloroacetic acid. The samples were centrifuged and the pelleted protein solubilized with 50 μl of 3M Tris base. The protein concentration of samples were determined by the method of Lowry O. H., Rosebrough N. J., Farr A. L., Randall R. J., *J Biol Chem* 1951;193:265–275. Protein samples (80 μg) were then subjected to SDS-polyacrylamide gel electrophoresis (SDS-PAGE) as described by Laemmli U. K., *Nature* 1970;331:315–319. The proteins were transferred from the gels to PVDF membranes (Western blot) as described by Towbin H., Staehelin T., Gordon J., *Proc Natl Acad Sci. USA* 1979;76:4350–4354. The blots were then probed with rabbit antibrain spectrin antibody (primary antibody) followed by alkaline phosphatase-conjugated goat antirabbit immunoglobulin G antibody (secondary antibody). Bands of spectrin (220 kDa) and its breakdown products (150 kDa, 145 kDa) were visualized by color development as described by Blake M. S., Johnson K. H., Russell-Jones G. J., Getschlich E. C., *Anal Biochem* 1984;36:175–179. The SBP were quantified by densitometry (BioRad Model 620).

Based on antispectrin staining of immunoblot of cortical cell samples, it was shown that control cells had only the intact spectrin (220 kDa) while NMDA treatment induced significant calpain-mediated formation of spectrin breakdown products (SBP) 150 kDa and 145 kDa. Again NMDA antagonist MK-801 inhibited the SBP formation. Examples of the thiol-acrylate Examples 3 and 22 partially blocked SBP formation, especially the 145 kDa fragment formation was reduced by 34% to 79%. Since the breakdown of spectrin is indicative of the eventual cell death, these results strongly suggest that the thiol-acrylates are protective against neuronal death.

Therefore, the compounds of Formula I and their pharmacologically acceptable salts are effective agents in the prophylaxis and/or therapeutic treatment of disorders responsive to agents which inhibit calcium-dependent neutral proteases, thus forming a further aspect of the present invention in like manner.

In view of the data presented the novel compounds of the instant invention are expected to be useful in the treatment of central nervous system disorders related to their biological activity. This includes alleviation, treatment, or elimination of an indication associated with the biological activity. This includes especially calpain-related psychosis, calpain-related anorexia, calpain-related ischemia, stroke, cerebral vasospasm, traumatic brain injury, and spinal cord and/or peripheral nerve injury. It also includes cardiac infarction, cataract, inflammation, restenosis, muscular dystrophy, and platelet aggregation.

Methods of synthesis of the compounds of the instant invention are illustrated in the following schemes. Generally, the preparation of compounds of Formula I above wherein $R^3$ and R are hydrogen and $R^1$ and $R^2$ are as defined above are prepared by the method shown in Scheme A.

Scheme A consists of treating a carbonyl compound (either an aldehyde or a ketone) of the general structure A with rhodanine in the presence of a weak nonnucleophilic base in an organic acid with or without an inert solvent to produce a thioxothiazolidinone of general structure B. The resulting thioxothiazolidione B is saponified with aqueous alkaline base, such as sodium hydroxide, potassium hydroxide or lithium hydroxide to produce the α-mercaptoacrylic acid of general structure C. By inert solvent is meant a nonpoetic solvent, such as for example, benzene, toluene, ether, tetrahydrofuran, or the like.

Alternatively, as shown in Scheme B, the carbonyl compounds of general Formula A can be reacted with a suitably protected α-mercaptoacetic acid of general structure D in the presence of a base in an inert solvent to produce the protected α-mercaptoacrylic acid esters of general Formula E wherein $R^8$ is a trialkylsilyl group and R is defined above (Ref: *Tetrahedron Lett* 1973;27:2461–2462). Suitable base for this condensation reaction include, for example such reagents as sodium hydride, lithium diisopropylamide (LDA), sodium methoxide. The compounds of general Structure E may be further reacted by treatment with fluoride to provide the compounds of general Formula F. Compounds F may be treated with hydroxide ion to provide the compounds of Structure C.

SCHEME A

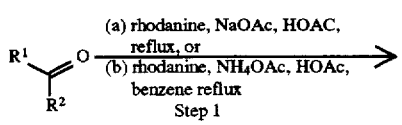

A

-continued
SCHEME A

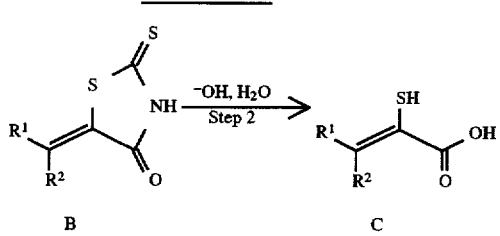

SCHEME B

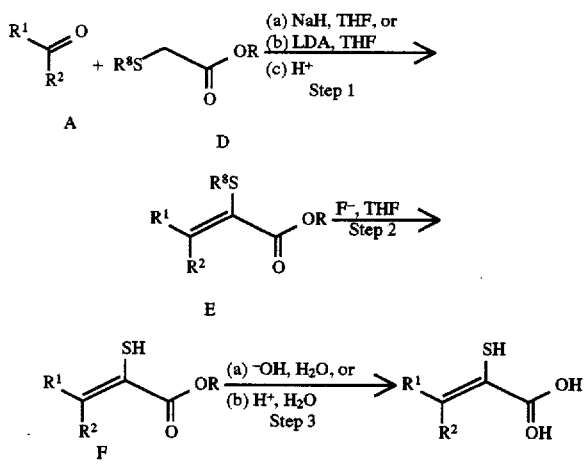

Further, preparation of compounds of the Formula I wherein R≠H and R¹ and R² are as previously defined are illustrated in Scheme C. Treatment of the carbonyl compounds of general Formula A with a suitably thiol protected α-mercaptoacetic acid ester of general Structure D in the presence of a base, such as, sodium hydride, lithium diisopropylamide (LDA) or sodium methoxide in an inert solvent may provide the protected α-mercaptoacrylic acid esters of general Formula E wherein R⁸ is a trialkylsilyl group and R is defined above. The compounds of general Structure E may be further reacted by treatment with fluoride or aqueous acid to provide the compounds of Formula F.

SCHEME C

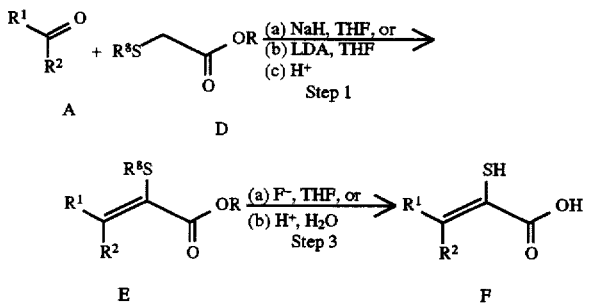

Starting materials for the processes described above are known or can be prepared by known processes.

The products of the reactions described herein are isolated by conventional means such as extraction, distillation, chromatography, and the like.

Variations within the processes described are within the skill of the art for the preparation of compounds of the Formula I.

EXAMPLE 1

Method A: 2-thioxo-4-thiazolidinone

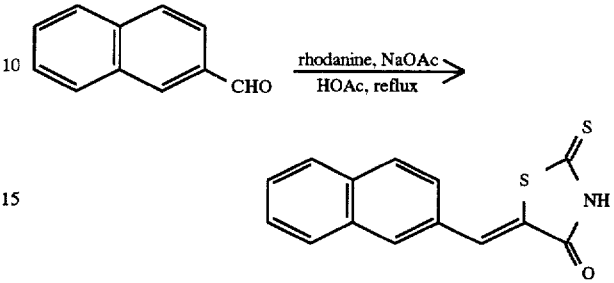

This compound was synthesized according to a procedure reported by Wagner, et al (Wagner J., Vitali P., Schoun J., Giroux E., Can J Chem 1977;55:4028). A solution of 2-naphthaldehyde (3.43 g, 21.96 mmol), rhodanine (2.92 g, 21.92 mmol), and sodium acetate (5.16 g, 62.91 mmol) in 35 mL of glacial acetic acid were refluxed for 2 hours. The reaction mixture was cooled to room temperature and water (30 mL) was added. The precipitates were collected by filtration then washed with water (5×60 mL). The orange-colored solid was air dried then it was washed with ether (2×30 mL) to give 5.17 g (87%) of an orange powder after air dried.

¹HNMR (300 MHz, DMSO-d₆) δ 13.88 (1H, s), 8.19 (1H, s), 8.08–7.96 (3H, m), 7.79 (1H, s), 7.69–7.58 (3H, m).

EXAMPLE 2

Method B: 2-thioxo-4-thiazolidinone

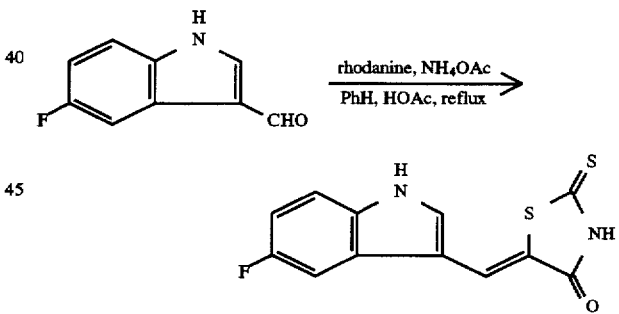

This compound was prepared by a modified procedure (Chakrabarti P. M., Chapman N. B., Clarke K., Tetrahedron 1969;25:2781). A suspension of 5-fluoroindole-3-carboxaldehyde (2.96 g, 18.14 mmol), rhodanine (2.39 g, 17.94 mmol), and ammonium acetate (1.56 g, 20.24 mmol) in 15 mL of glacial acetic acid, and 30 mL of benzene was refluxed under azeotropic conditions. The suspension turned into a yellow solution after 5 minutes and then turned into a thick orange suspension after refluxed for 15 minutes. Benzene (60 mL) was then added to the reaction mixture and the yellow suspension was refluxed for another 2 hours. The reaction mixture was cooled to room temperature and the orange solid was collected by filtration. The solid was washed with water (3×100 mL) followed by ether (2×60 mL) to give 4.74 g (95%) of the desired product as an orange powder.

$^1$HNMR (300 MHz, DMSO-d$_6$) δ 13.57 (1H, s), 12.38 (1H, s), 7.94 (1H, s), 7.87 (1H, d, J=3.05 Hz), 7.81 (1H, dd, J=9.92, 2.29 Hz), 7.50 (1H, dd, J=8.82, 4.55 Hz), 7.10 (1H, dt, J=9.11, 2.34 Hz).

EXAMPLE 3

Method C: (Z)-2-Propenoic Acid, 2-mercapto-3-(7-naphthalenyl)

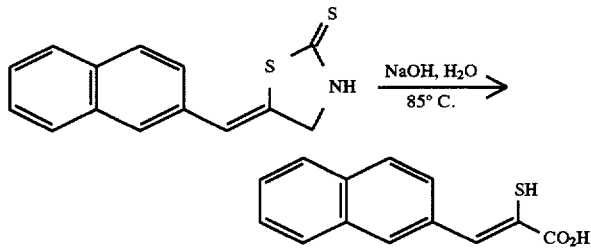

To a solution of sodium hydroxide (1.00 g, 25.00 mmol) in 25 mL of water was added the 2-thioxo-4-thiazolidinone (1.53 g, 5.64 mmol). The suspension was heated at 85° C. under argon for 1.5 hours. The orange suspension turned into a yellow solution after 15 minutes at 85° C. At the end of the 1.5 hours period, the reaction mixture was cooled to room temperature then washed with ether (20 mL). The aqueous layer was then collected and acidified at 0° C. with concentrated hydrochloric acid to pH=1. The precipitates were collected and washed with water (4×60 mL). The solid was then air dried. The yellow solid was then dissolved in 30 mL of warm methanol. Water (30 mL) was added to precipitate out the product. The light yellow precipitates were collected by filtration and dried overnight in vacuum at 70° C. to give 0.39 g (30%) of the desired product as a pale yellow powder, mp=167°–169° C.

Anal. Calc. for C$_{13}$H$_{10}$O$_2$S: C, 67.80; H, 4.38; N, 0.00. Found: C, 67.88; H, 4.33; N, 0.00.

EXAMPLE 4

Method D: 3-(5-fluoro-3-indolyl)-2-mercapto-2-propenoic Acid

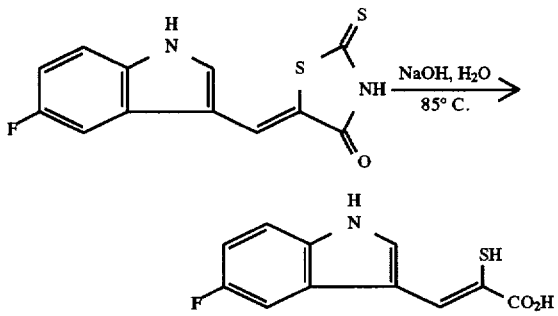

To a solution of sodium hydroxide (3.10 g, 77.50 mmol) in 68 mL of water was added the 2-thioxo-4-thiazolidinone (2.25 g, 8.08 mmol). The suspension was heated at 85° C. in an argon atmosphere for 3 hours. The orange suspension turned into a red solution after 15 minutes at 85° C. At the end of the 3-hour period, the reaction mixture was cooled to room temperature then washed with ether (2×30 mL). The aqueous layer was then collected and acidified at 0° C. with concentrated hydrochloric acid to pH=1. The yellow solid was collected by filtration and washed with water (4×60 mL). The solid was then dissolved in 200 mL of ether and extracted with saturated sodium carbonate solution (50 mL). The aqueous layer was collected and acidified with concentrated hydrochloric acid at 0° C. to pH=1. The solid was dissolved in 200 mL of ether, washed with water (2×100 mL), then the organic layer was dried with anhydrous magnesium sulphate. The mixture was filtered, and the residue was washed with ethyl acetate (2×10 mL). The filtrate was concentrated on a rotavap and the solid obtained was triturated with 1:5 ether:hexanes (50 mL) and then collected by filtration. The yellow solid was washed with hexanes (2×60 mL) and air dried to give 0.85 g (44%) of the thiolacrylic acid as an orange powder.

$^1$HNMR (300 MHz, DMSO-d$_6$) δ 13.10 (1H, br s), 11.93 (1H, s), 8.01 (1H, s), 8.00 (1H, s), 7.55 (2H, m), 7.06 (1H, dt, J=9.13, 2.43 Hz), 5.09 (1H, br s).

EXAMPLE 5

Ethyl (trimethylsilylthio)acetate

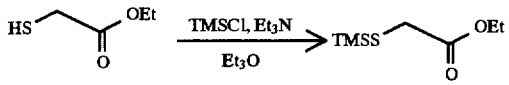

To a solution of ethyl mercaptoacetate (9.0 mL, 83.2 mmol) in 15 mL of anhydrous ether under nitrogen atmosphere was added trimethylsilyl chloride (12.0 mL, 94.6 mmol) followed by triethyl amine (13.0 mL, 93.3 mmol) slowly. White precipitates were formed upon addition of triethyl amine. The suspension was allowed to stir at room temperature overnight. The white precipitate was removed by filtration. The filtrate was concentrated on a rotavap. The residue oil was distilled at 40° C. (0.5 mm Hg) to give 10.9 g (68%) of ethyl (trimethylsilylthio)acetate as a colorless oil.

$^1$HNMR (300 MHz, CDCl$_3$) δ 4.18 (2H, q, J=7.19 Hz), 3.20 (2H, s), 1.29 (3H, t, J=7.12 Hz), 0.35 (9H, s).

EXAMPLE 6

Ethyl 2-Propenoic Acid, (Z)-2-mercapto-3-(2-naphthalenyl)-, Ethyl Ester

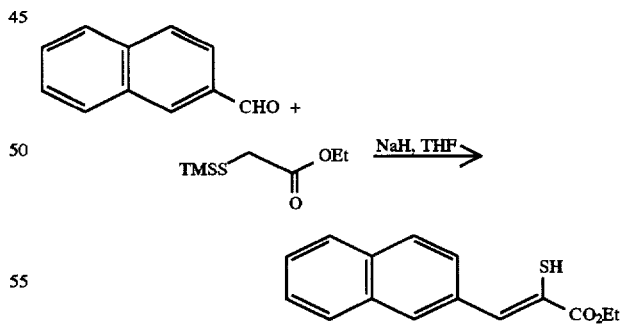

This compound was synthesized by a modified procedure (Tetrahedron Lett 1973;27:2461). To a solution of 2-naphthaldehyde and ethyl mercaptoacetate in 25 mL of anhydrous tetrahydrofuran was added sodium hydride. The reaction mixture was allowed to stir at room temperature in an argon atmosphere for 6 hours. The mixture was poured into 140 mL of ether and allowed to stand at room temperature for 30 minutes. The resulting precipitates were filtered. The filtrate was extracted repeatedly with water (4×60 mL).

The aqueous layer was collected and acidified with hydrochloric acid. The solution was concentrated under reduced pressure to give a yellow precipitate. The precipitate was collected and dissolved in a small amount of ether. The resulting solution was then chromatographed on silica gel using 30% ether in hexanes to give 0.13 g (2.8%) of the ester as an off-white solid.

Anal. Calc. for $C_{15}H_{14}O_2S$: C, 69.74; H, 5.46; N, 0.00. Found: C, 69.44;,H, 5.41; N, 0.00.

EXAMPLE 7

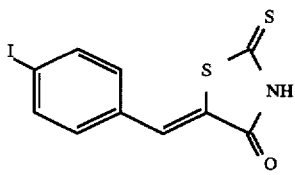

Method B was used to synthesize this compound from 4-iodobenzaldehyde in 66% yield.

$^1$HNMR (250 MHz, DMSO-$d_6$) δ 13.89 (1H, br s), 7.91 (2H, d, J=8.33 Hz), 7.59 (1H, s), 7.38 (2H, d, J=8.33 Hz).

EXAMPLE 8

(Z)-2-propenoic Acid, 3-(4-iodophenyl)-2-mercapto

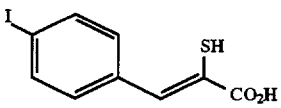

Method C was used to synthesize this compound. The product was recrystallized from methanol (24% yield), mp=189°–191° C.

Anal. Calc. for $C_9H_7IO_2S$: C, 35.31; H, 2.30; N, 0.00, S 10.47. Found: C, 35.37; H, 2.39; N, 0.00, S 10.47.

EXAMPLE 9

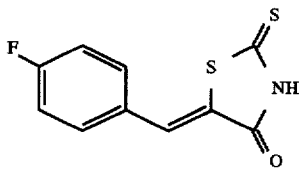

Method B was used to synthesize this compound from 4-fluorobenzaldehyde in 66% yield.

Anal. Calc. for $C_{10}H_6FNOS_2$: C, 50.19; H, 2.53; N, 5.85. Found: C, 49.99; H, 2.50; N, 5.70.

EXAMPLE 10

2-Propenoic Acid, 3-(4-fluorophenyl)-2-mercapto

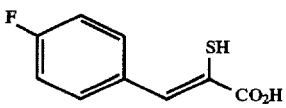

Method C was used to synthesize this compound in 32% yield.

Anal. Calc. for $C_9H_7FO_2S$: C, 54.54; H, 3.56; N, 0.00. Found: C, 54.15; H, 3.43; N, 0.00.

EXAMPLE 11

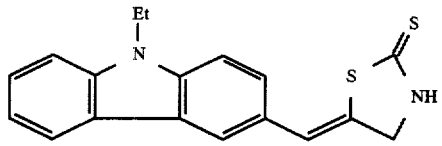

Method A was used to synthesize this compound from 9-ethyl-3-carbazolecarbox-aldehyde in 69% yield.

$^1$HNMR (300 MHz, DMSO-$d_6$) δ 13.75 (1H, br s), 8.40 (1H, s), 8.26 (1H, d, J=7.93 Hz), 7.83 (1H, s), 7.78 (1H, d, J=8.68 Hz), 7.68 (2H, m), 7.54 (1H, t, J=7.63 Hz), 7.29 (1H, t, J=7.33 Hz), 4.48 (2H, q, J=7.07 Hz), 1.33 (3H, t, J=7.02 Hz).

EXAMPLE 12

(Z)-2-Propenoic Acid, 3-(9-ethyl-9H-carbazol-2-yl)-2-mercapto

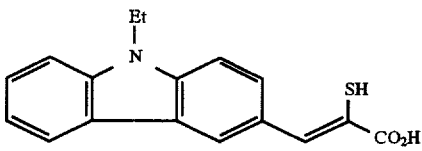

Method C was used to synthesize this compound in 20% yield, mp=191°–192° C.

EXAMPLE 13

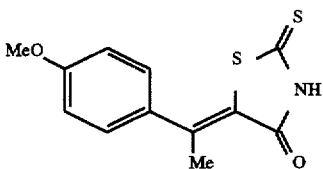

Method A was used to synthesize this compound from 4'-methoxyacetophenone in 42% yield.

$^1$HNMR (300 MHz, DMSO-$d_6$) δ 13.48 (1H, br s), 7.45 (2H, d, J=8.82 Hz), 7.05 (2H, d, J=8.75 Hz), 3.82 (3H, s), 2.65 (3H, s).

EXAMPLE 14

(Z)-2-Butanoic Acid, 2-mercapto-3-(4-methoxyphenyl)

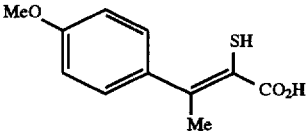

Method C was used to synthesize this compound in 51% yield, mp=143°–144° C.

Anal. Calc. for $C_{11}H_{12}O_3S$: C, 58.91; H, 5.39; N, 0.00, S, 14.30. Found: C, 58.67; H, 5.33; N, 0.00, S 14.23.

EXAMPLE 15

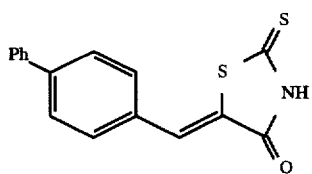

Method A was used to synthesize this compound from 4-biphenylcarboxaldehyde in 83% yield.

Anal. Calc. for $C_{16}H_{11}NOS_2$: C, 64.62; H, 3.73; N, 4.71. Found: C, 64.52; H, 3.66; N, 4.47.

EXAMPLE 16

(Z)-2-Propenoic Acid, 3-[1,1'-biphenyl)-4-yl-2-mercapto

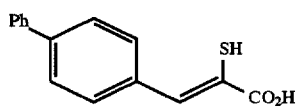

Method C was used to synthesize this compound in 44% yield, mp=198°–200° C.

Anal. Calc. for $C_{15}H_{12}O_2S$: C, 70.29; H, 4.72; N, 0.00, S, 12.51. Found: C, 69.94; H, 4.59; N, 0.00, S 12.19.

EXAMPLE 17

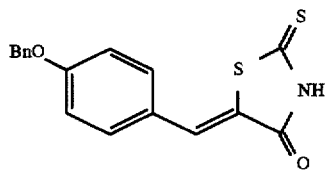

Method A was used to synthesize this compound from 4-benzyloxybenzaldehyde in 72% yield.

$^1$HNMR (300 MHz, DMSO-d$_6$) δ 13.77 (1H, br s), 7.61 (1H, s), 7.57 (2H, d, J=8.75 Hz), 7.48–7.32 (5H, m), 7.19 (2H, d, J=8.88 Hz), 5.20 (2H, s).

EXAMPLE 18

(Z)-2-Propenoic Acid, 2-mercapto-3-[4-(phenylmethoxy)phenyl]

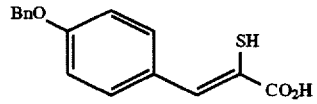

Method C was used to synthesize this compound in 57% yield, mp=178°–180° C.

Anal. Calc. for $C_{16}H_{14}O_3S$: C, 67.11; H, 4.93; N, 0.00, S, 11.20. Found: C, 66.81; H, 4.86; N, 0.00, S 11.09.

EXAMPLE 19

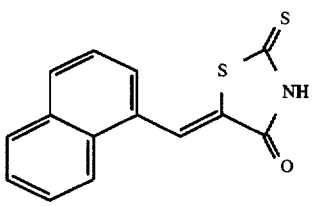

Method A was used to synthesize this compound from 1-naphthaldehyde in 60% yield.

$^1$HNMR (300 MHz, DMSO-d$_6$) δ 13.88 (1H, br s), 8.30 (1H, s), 8.18 (1H, d, J=7.93 Hz), 8.11–8.03 (2H, m), 7.68 (4H, m).

EXAMPLE 20

(Z)-2-Propenoic Acid, 2-mercapto-3-(1-naphthalenyl)

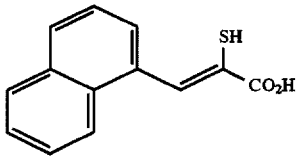

Method C was used to synthesize this compound in 57% yield, mp=182°–184° C.

Anal. Calc. for $C_{16}H_{14}O_3S$: C, 67.80; H, 4.38; N, 0.00, S, 13.92. Found: C, 67.11; H, 4.43; N, 0.00, S 13.95.

EXAMPLE 21

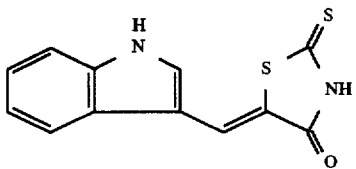

Method A was used to synthesize this compound from indole-3-carboxaldehyde in 63% yield.

Anal. Calc. for $C_{12}H_8N_2OS_2$: C, 55.36; H, 3.10; N, 10.76, S, 24.63. Found: C, 55.41; H, 3.09; N, 10.96, S 24.56.

EXAMPLE 22

(Z)-2-Propenoic Acid, 3-(1H-indol-3-yl)-2-mercapto

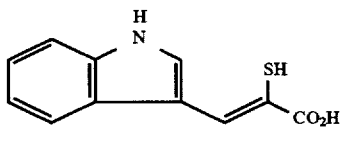

Method C was used to synthesize this compound in 44% yield, mp=172°–174° C.

$^1$HNMR (300 MHz, DMSO-d$_6$) δ 13.17 (1H, br s), 11.85 (1H, s), 8.07 (1H, s), 7.95 (1H, d, J=2.51 Hz), 7.75 (1H, d, J=7.93 Hz), 7.49 (1H, δ J=8.27 Hz), 7.25–7.13 (2H, m), 5.10 (1H, br s).

EXAMPLE 23

Indole-2-carboxaldehyde

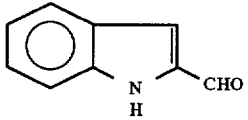

To a solution of ethyl indole-2-carboxylate (8.50 g, 44.9 mmol) in 100 mL of anhydrous THF under nitrogen atmosphere at 0° C. was added a 1M solution of lithium aluminium hydride in THF (54 mL, 54 mmol). The reaction mixture was stirred at 0° C. for 45 minutes and then quenched by the sequential addition of water (2 mL), 15% sodium hydroxide solution (2 mL), and water (6 mL). The mixture was filtered through a pad of Celite. The residue was washed with THF (2×50 mL) and ether (2×50 mL). The filtrate was dried with anhydrous magnesium sulphate, filtered, and concentrated under reduced pressure to give 6.19 g of a brown solid. The solid was then dissolved in 365 mL of anhydrous methylene chloride and activated manganese dioxide (48.2 g, 0.55 mol) was added. The reaction mixture was stirred vigorously at room temperature for 2 hours. At the end of the 2-hour period, the mixture was filtered through a pad of Celite to remove excess manganese dioxide. The filtrate was washed with hot acetone (4×100 mL). The filtrate was concentrated to give 4.11 g (65%) of the aldehyde as a brown solid.

$^1$HNMR (200 MHz, DMSO-$d_6$) δ 9.86 (1H, s), 9.20 (1H, br s), 7.76 (1H, d, J=8.12 Hz), 7.55–7.10 (4H, m).

EXAMPLE 24

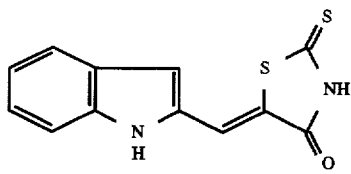

Method A was used to synthesize this compound from indole-2-carboxaldehyde in 73% yield.

$^1$HNMR (200 MHz, DMSO-$d_6$) δ 13.80 (1H, br s), 11.72 (1H, s), 7.69 (1H, d, J=8.12 Hz), 7.81 (1H, s), 7.48 (1H, d, J=8.22 Hz), 7.26 (1H, t, J=7.48 Hz), 7.10 (1H, d, J=7.48 Hz), 6.88 (1H, s).

EXAMPLE 25

3-(2-indolyl)-2-mercapto-2-propenoic Acid

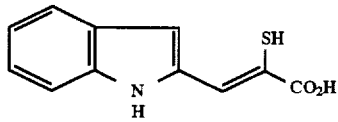

Method C was used to synthesize this compound in 30% yield, mp=154°–156° C.

Anal. Calc. for $C_{11}H_9NO_2S$: C, 60.26; H, 4.14; N, 6.39. Found: C, 60.61; H, 4.02; N, 6.36.

EXAMPLE 26

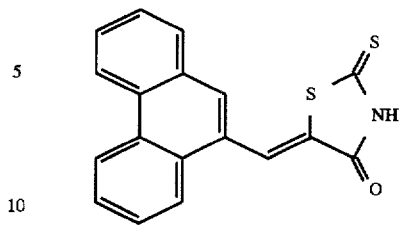

Method A was used to synthesize this compound from phenanthrene-9-carboxaldehyde in 61% yield.

$^1$HNMR (300 MHz, DMSO-$d_6$) δ 13.95 (1H, br s), 8.94 (1H, d, J=7.80 Hz), 8.87 (1H, d, J=8.41 Hz), 8.28 (1H, s), 8.17 (2H, t, J=8.55 Hz), 8.02 (1H, s), 7.83–7.65 (4H, m).

EXAMPLE 27

3-(9--phenanthyl)-2-mercapto-2-propenoic Acid

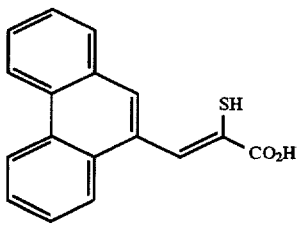

Method C was used to synthesize this compound in 82% yield, mp=192°–194° C.

Anal. Calc. for $C_7H_{12}O_2S$: C, 72.83; H, 4.31; N, 0.00. Found: C, 72.49; H, 4.36; N, 0.00.

EXAMPLE 28

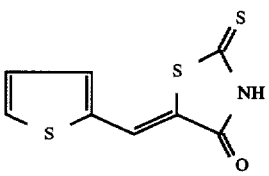

Method A was used to synthesize this compound from thiophene-2-carboxaldehyde in 87% yield.

$^1$HNMR (200 MHz, DMSO-$d_6$) δ 13.68 (1H, br s), 8.08 (1H, d, J=4.80 Hz), 7.92 (1H, s), 7.71 (1H, d, J=3.09 Hz), 7.30 (1H, m).

EXAMPLE 29

(Z)-2-Propenoic Acid, 3-(2-thienyl)-3-mercapto

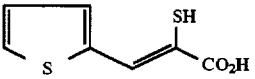

Method C was used to synthesize this compound in 89% yield, mp=146°–148° C.

Anal. Calc. for $C_7H_6O_2S_2$: C, 45.15; H, 3.25; N, 0.00. Found: C, 44.87; H, 3.09; N, 0.00.

EXAMPLE 30

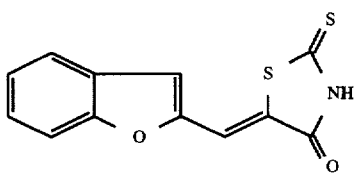

Method A was used to synthesize this compound from benzofuran-2-carboxaldehyde in 84% yield.

Anal. Calc. for $C_{12}H_7NO_2S_2$: C, 55.16; H, 2.70; N, 5.36. Found: C, 55.10; H, 2.63; N, 5.14.

EXAMPLE 31

(Z)-2-Propenoic Acid, 3-(2-benzofuranyl)-2-mercapto

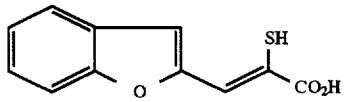

Method C was used to synthesize this compound in 66% yield, mp=191°–193° C.

Anal. Calc. for $C_{11}H_8O_3S$: C, 59.99; H, 3.66; N, 0.00. Found: C, 59.91; H, 3.78; N, 0.00.

EXAMPLE 32

6-bromo-2-naphthaldehyde

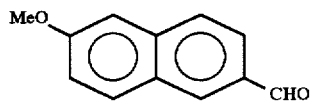

To a solution of 2-bromo-6-methoxynaphthalene (4.00 g, 16.87 mmol) in 100 mL of anhydrous THF under nitrogen atmosphere at −78° C. was added a 1.6M solution of n-butyllithium in hexane (10.6 mL, 16.96 mmol). The reaction mixture turned into a yellow suspension 5 minutes after the addition of butyllithium. The suspension was stirred at −78° C. for 1 hour and then warmed to −23° C. Anhydrous N,N-dimethylformamide (4.0 mL, 51.7 mmol) was added. The reaction mixture was stirred at −23° C. for 30 minutes. Saturated sodium chloride solution (50 mL) was added to quench the reaction. The organic layer was collected and the aqueous layer was extracted with ethyl acetate (2×50 mL). The combined organic layers were dried with anhydrous magnesium sulphate, filtered, and concentrated under reduced pressure. The residue oil was chromatographed by 10% ethyl acetate in hexanes on silica gel to give 2.86 g (91%) of 6-methoxy-2-naphthaldehyde as a white solid.

$^1$HNMR (300 MHz, CDCl$_3$) δ 10.10 (1H, s), 8.26 (1H, s), 7.95–7.78 (3H, m), 7.28–7.18 (2H, m), 3.97 (3H, s).

EXAMPLE 33

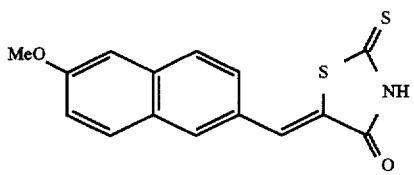

Method A was used to synthesize this compound from 6-methoxy-2-naphthaldehyde in 86% yield.

$^1$HNMR (300 MHz, DMSO-d$_6$) δ 13.85 (1H, s), 8.12 (1H, s), 7.99 (1H, d, J=9.09 Hz), 7.95 (1H, d, J=8.68 Hz), 7.75 (1H, s), 7.63 (1H, dd, J=8.36, 1.80 Hz), 7.40 (1H, d, J=2.37 Hz), 7.26 (1H, dd, J=8.99, 2.48 Hz), 3.92 (3H,s).

EXAMPLE 34

(Z)-2-Propenoic Acid, 2-mercapto-3-(6-methoxy-2-naphthalenyl)

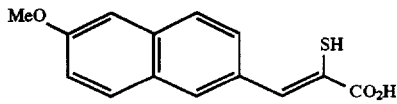

Method C was used to synthesize this compound in 66% yield, mp=181°–183° C.

Anal. Calc. for $C_{14}H_{12}O_3S$: C, 64.60; H, 4.65; N, 0.00. Found: C, 64.66; H, 4.42; N, 0.00.

EXAMPLE 35

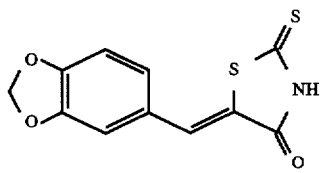

Method A was used to synthesize this compound from piperonal in 88% yield.

$^1$HNMR (200 MHz, DMSO-d$_6$) δ 13.80 (1H, br s), 7.59 (1H, s), 7.15 (3H, m), 6.16 (2H,s).

EXAMPLE 36

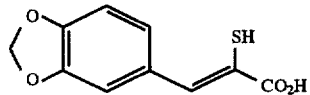

Method C was used to synthesize this compound in 66% yield, mp=197°–198° C.

Anal. Calc. for $C_{10}H_7O_4S$: C, 53.81; H, 3.16; N, 0.00. Found: C, 53.60; H, 3.57; N, 0.00.

EXAMPLE 37

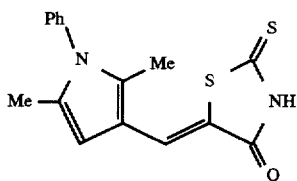

Method A was used to synthesize this compound from 2,5-dimethyl-1-phenylpyrrole-3-carboxaldehyde in 71% yield.

$^1$HNMR (300 MHz, DMSO-d$_6$) δ 13.46 (1H, s), 7.55 (3H, m), 7.53 (1H, s), 7.36 (2H, d, J=7.05 Hz), 6.19 (1H, s), 2.13 (3H, s), 1.99 (3H, s).

EXAMPLE 38

(Z)-2-Propenoic Acid, 3-(2,5-dimethyl-1-phenyl-1H-pyrrol-3-yl)-2-mercapto

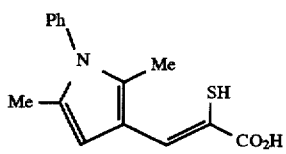

Method C was used to synthesize this compound in 42% yield, mp=182°–183° C.

$^1$HNMR (300 MHz, DMSO-d$_6$) δ 12.82 (1H, br s), 7.69 (1H, s), 7.53 (3H, m), 7.32 (2H, d, J=7.05 Hz), 6.57 (1H,s), 4.79 (1H, br s), 2.04 (3H, s), 2.00 (3H, s).

EXAMPLE 39

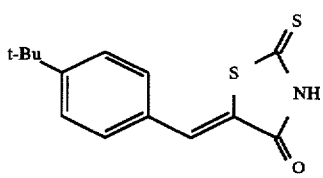

Method A was used to synthesize this compound from 4-tert-butylbenzaldehyde in 89% yield. Hexanes was used instead of ether in the final wash.

$^1$HNMR (300 MHz, DMSO-d$_6$) δ 13.83 (1H, br s), 7.63 (1H, s), 7.56 (4H, m), 1.30 (9H, s).

EXAMPLE 40

(Z)-2-propenoic Acid, 3-[4-(1,1-dimethylethyl)phenyl]-2-mercapto

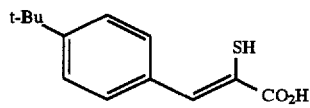

To a solution of sodium hydroxide (3.43 g, 85.75 mmol) in 80 mL of water was added the 2-thioxo-4-thiazolidinone (2.32 g, 83.63 mmol). The suspension was heated at 85° C. under argon for 5 hours. The reaction mixture was cooled to room temperature then washed with ether (40 mL). The aqueous layer was then collected and acidified at 0° C. with concentrated hydrochloric acid to pH=1. Ether (40 mL) was added to dissolve the yellow oil. The ether layer was collected and the aqueous layer was washed again with ether (2×40 mL). The combined organic extracts were dried with anhydrous magnesium sulphate, filtered, and concentrated to give a yellow solid. Hexane (100 mL) was added to the solid and the mixture was stirred vigorously under argon atmosphere for 1 hour. The remaining solid was removed by filtration. The filtrate was concentrated down to approximately 20 mL in volume. The solution was then cooled to −23° C. to precipitate out the product. The precipitates were collected by filtration and air dried to give 0.30 g (15%) of the desired product as a white powder, mp=143°–144° C.

$^1$HNMR (200 MHz, CDCl$_3$) δ 10.20 (1H, br s), 7.93 (1H, s), 7.66 (2H, d, J=8.55 Hz), 7.49 (2H, d, J=8.35 Hz), 4.66 (1H, s), 1.35 (9H, s).

EXAMPLE 41

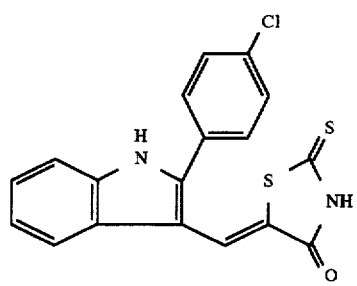

Method B was used to synthesize this compound from 2-(4-chlorophenyl)indole-3-carboxaldehyde in 84% yield.

$^1$HNMR (300 MHz, DMSO-d$_6$) δ 13.57 (1H, s), 12.50 (1H, s), 7.84 (1H, d, J=7.80 Hz), 7.78 (1H, s), 7.66 (4H, m), 7.52 (1H, d, J=7.94 Hz), 7.28 (2H, m).

EXAMPLE 42

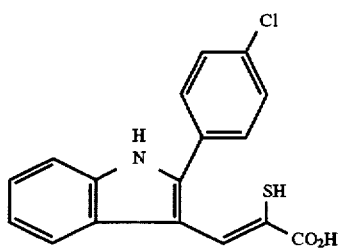

Method C was used to synthesize this compound in 38% yield, mp=197°–198° C.

$^1$HNMR (300 MHz, DMSO-d$_6$) δ 13.20 (1H, br s), 11.99 (1H, s), 7.87 (1H, s), 7.62–7.54 (5H, m), 7.47 (1H, d, J=7.60 Hz), 7.24–7.09 (2H, m), 4.35 (1H, br s).

EXAMPLE 43

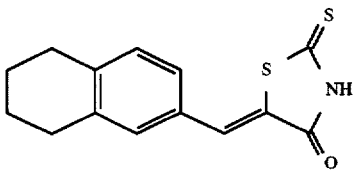

Method B was used to synthesize this compound from 1,2,3,4-tetrahydro-6-naphthaldehyde in 92% yield.

$^1$HNMR (300 MHz, DMSO-$d_6$) δ 13.78 (1H, br s), 7.53 (1H, s), 7.24 (3H, m), 2.75 (4H, br s), 1.74 (4H, br s).

EXAMPLE 44

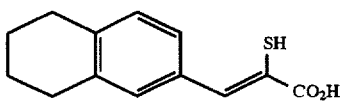

Method C was used to synthesize this compound in 27% yield. The final ether wash was skipped for this preparation. mp=145°–147° C.

Anal. Calc. for $C_{13}H_{14}O_2S$: C, 66.64; H, 6.02; N, 0.00; S, 13.68. Found: C, 66.70; H, 6.08; N, 0.00; S, 13.28.

EXAMPLE 45

4-(phenethyl)benzaldehyde

To a solution of 4-stilbenecarboxaldehyde (5.14 g, 24.68 mmol) in 125 mL of ethyl acetate was added 0.13 g of 5% Pd/C catalyst. The reaction was stirred under hydrogen (1 atm) for 2 hours. An additional 0.14 g of 5% Pd/C catalyst was added and the reaction mixture was stirred under hydrogen (1 atm) again for 1 hour. The catalyst was removed by filtration through a pad of Celite. The residue was washed with ethyl acetate (2×30 mL) and the filtrate was concentrated on a rotavap. The residue oil was chromatographed with 15% ethyl acetate in hexanes on silica gel to give 2.62 g (50%) of the desired product as a white solid.

$^1$HNMR (300 MHz, CDCl$_3$) δ 9.99 (1H, s), 7.81 (2H, d, J=8.14 Hz), 7.35–7.15 (7H, m), 2.99 (4H, m).

EXAMPLE 46

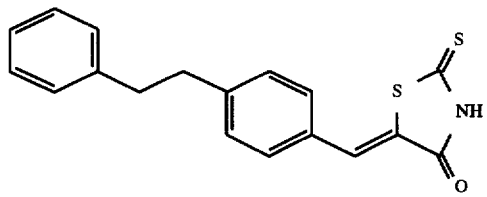

Method B was used to synthesize this compound from 4-(phenethyl)benzaldehyde in 92% yield.

$^1$HNMR (300 MHz, DMSO-$d_6$) δ 13.82 (1H, br s), 7.61 (1H, s), 7.50 (2H, d, J=6.85 Hz), 7.39 (2H, d, J=8.07 Hz), 7.23 (5H, m), 2.91 (4H, br s).

EXAMPLE 47

(Z)-2-Propenoic Acid, 2-mercapto-3-[4-(2-phenylethyl)-phenyl]

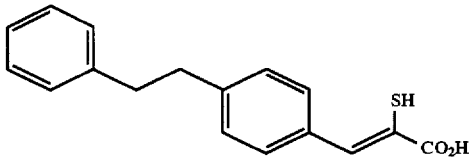

Method C was used to synthesize this compound in 21% yield. The final ether wash was skipped for this preparation. mp=153°–155° C.

Anal. Calc. for $C_{17}H_{16}O_2S$: C, 71.80; H, 5.67; N, 0.00. Found: C, 72.16; H, 5.76; N, 0.00.

EXAMPLE 48

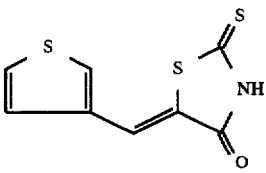

Method A was used to synthesize this compound from 3-thiophenecarboxaldehyde in 80% yield.

$^1$HNMR (200 MHz, DMSO-$d_6$) δ 13.80 (1H, br s), 8.10 (1H, s), 7.50 (2H, d, J=6.85 Hz), 7.39 (2H, d, J=8.07 Hz), 7.23 (5H, m), 2.91 (4H, br s).

EXAMPLE 49

(Z)-2-Propenoic Acid, 3-(3-thienyl)-2-mercapto

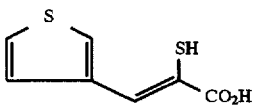

Method C was used to synthesize this compound in 46% yield. The final ether wash was skipped for this preparation.

Anal. Calc. for $C_7H_6O_2S_2$: C, 45.14; H, 3.25; N, 0.00. Found: C, 45.14; H, 3.22; N, 0.00.

EXAMPLE 50

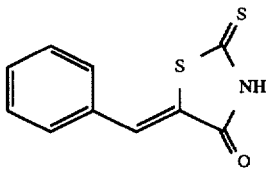

Method B was used to synthesize this compound from benzaldehyde in 76% yield.

$^1$HNMR (300 MHz, DMSO-d6) δ 13.82 (1H, br s), 7.65 (1H, s), 7.59–7.46 (5H, m).

EXAMPLE 51

2-Propenoic Acid, 2-mercapto-3-phenyl

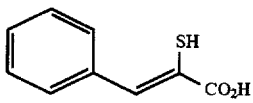

Method C was used to synthesize this compound in 47% yield. The final ether-wash was skipped for this preparation.

$^1$HNMR (300 MHz, DMSO-$d_6$) δ 13.40 (1H, br s), 7.75 (1H, s), 7.69 (2H, d, J=7.46 Hz), 7.52–7.20 (3H, m), 5.20 (1H, br s).

EXAMPLE 52

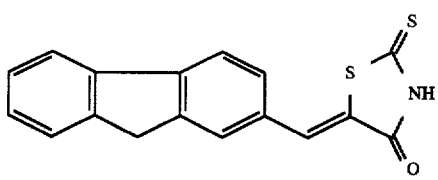

Method A was used to synthesize this compound from 2-fluorenecarboxaldehyde in 82% yield.

$^1$HNMR (300 MHz, DMSO-$d_6$) δ 13.84 (1H, br s), 8.05 (1H, d, J=8.00 Hz), 7.98 (1H, dd, J=7.80, 1.76 Hz), 7.78 (1H, s), 7.71 (1H, s), 7.63 (2H, d, J=6.71 Hz), 7.41 (2H, m), 4.01 (2H, s).

EXAMPLE 53

2-Propenoic Acid, 3-(9H-fluoren-2-yl)-2-mercapto

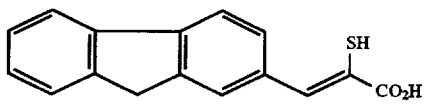

Method C was used to synthesize this compound in 21% yield. The final ether wash was skipped for this preparation.

$^1$HNMR (300 MHz, DMSO-$d_6$) δ 13.48 (1H, br s), 8.20–7.34 (8H, m), 4.00 (2H, s), 5.38 (1H, br s).

We claim:

1. A compound of Formula

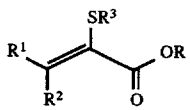

I or a pharmaceutically acceptable salt thereof wherein

R is hydrogen,
  alkyl,
  cycloalkyl,
  alkenyl,
  cycloalkenyl,
  alkynyl,
  aminoalkyl,
  aryl, or
  together with $R^3$ forms a ring;

$R^1$ is aryl with the proviso that aryl is not phenyl, or substituted phenyl, $R^1$ is substituted or unsubstituted heterocycle, with the proviso that heterocycle is not furan, thiophene, indole or pyrrole, $R^1$ is substituted or unsubstituted heterocyclealkyl, $R^1$ is substituted or unsubstituted heterocyclealkenyl, $R^1$ is substituted or unsubstituted heterocyclealkynyl, $R^2$ is hydrogen, alkyl of one, three, four, five or six carbon atoms, cycloalkyl, alkenyl, cycloalkenyl, alkynyl, aryl, arylalkyl, arylalkenyl, arylalkyl, arylalkenyl, or arylalkynyl and $R^3$ is hydrogen,
  alkyl,
  cycloalkyl,
  alkenyl,
  cycloalkenyl,
  alkynyl,
  aminoalkyl,
  aryl, or
  —$COR^4$ wherein $R^4$ is alkyl, alkenyl, alkynyl, alkoxy, amino, or aryl.

2. A compound according to claim 1 wherein

R is hydrogen or alkyl;

$R^1$ is substituted or unsubstituted heterocycle with the proviso that the heterocycle is not furan, thiophene, indole or pyrrole;

$R^2$ is hydrogen or alkyl of one, three, four, five or six carbon atoms; and $R^3$ is hydrogen
  alkyl,
  cycloalkyl,
  alkenyl,
  cycloalkenyl,
  alkynyl,
  aminoalkyl,
  aryl, or
  —$COR^4$ wherein $R^4$ is alkyl, alkenyl, alkynyl, alkoxy, amino, or aryl.

3. A compound according to claim 1 wherein

R is hydrogen or alkyl of from one to three carbon atoms;
$R^1$ is naphthyl,

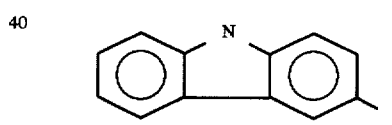

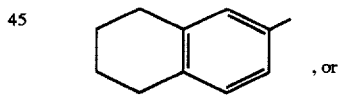

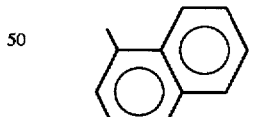

$R^2$ is hydrogen; and
$R^3$ is hydrogen.

4. A compound according to claim 1 named 3-(2-naphthyl)-2-mercapto-2-propenoic acid.

5. A compound according to claim 1 named (Z)-2-propenoic acid, 3-(9-ethyl-9H-carbazol-2-yl)-2-mercapto.

6. A compound according to claim 1 named (Z)-2-propenoic acid, 2-mercapto-3-(5,6,7,8-tetrahydro-2-naphthalenyl).

7. A compound according to claim 1 named ethyl-2-naphthyl-2-mercapto-2-propenoate.

8. A compound according to claim 1 named 3-(1-naphthyl)-2-mercapto-2-propenoic acid.

9. A pharmaceutical composition comprising a therapeutically effective amount of a compound according to claim 1 together with a pharmaceutically acceptable carrier in unit dosage form.

10. A method for treating neurodegenerative disorders which comprises administering to a mammal in need of such treatment a compound according to claim 1.

11. A method for treating stroke which comprises administering to a mammal in need of such treatment a compound according to claim 1.

12. A method for treating traumatic brain injury which comprises administering to a mammal in need of such treatment a compound according to claim 1.

13. A method for treating restenosis which comprises administering to a mammal in need of such treatment a compound according to claim 1.

14. A method for treating neurodegenerative disorders which comprises administering to a mammal in need of such treatment a compound selected from:

(Z)-2-propenoic acid, 2-mercapto-3-[4-(phenylmethoxy)phenyl];

3-(4-iodophenyl)-2-mercapto-2-propenoic acid;

(Z)-2-propenoic acid, 3-[1,1'-biphenyl]-4-yl-2-mercapto;

(Z)-2-propenoic acid, 2-mercapto-3-(9-phenanthienyl);

(Z)-2-propenoic acid, 3-(2,5-dimethyl-1-phenyl-1H-pyrrol-3-yl)-2-mercapto;

(Z)-2-propenoic acid, 3-[4-(1,1-dimethylethyl)phenyl]-2-mercapto;

(Z)-2-propenoic acid, 2-mercapto-3-[4-2-phenylethyl)phenyl];

(Z)-2-propenoic acid, 3-(3-thienyl)-2-mercapto; and (Z)-2-propenoic acid, 3-[2-(4-chlorophenyl)-1H-indol-3-yl]-2-mercapto.

15. A method for treating stroke which comprises administering to a mammal in need of such treatment a compound selected from:

(Z)-2-propenoic acid, 2-mercapto-3-[4-(phenylmethoxy)phenyl];

3-(4iodophenyl)-2mercapto-2-propenoic acid;

(Z)-2-propenoic acid, 3-[1,1'-biphenyl]-4-yl-2-mercapto;

(Z)-2-propenoic acid, 2-mercapto-3-(9-phenanthienyl);

(Z)-2-propenoic acid, 3-(2,5-dimethyl-1-phenyl-1H-pyrrol-3-yl)-2-mercapto;

(Z)-2-propenoic acid, 3-[4-(1,1-dimethylethyl)phenyl]-2-mercapto;

(Z)-2-propenoic acid, 2-mercapto-3-[4-(2-phenylethyl)phenyl];

(Z)-2-propenoic acid, 3-(3-thienyl)-2-mercapto; and (Z)-2-propenoic acid, 3-[2-(4-chlorophenyl)-1H-indol-3-yl]-2-mercapto.

16. A method for treating traumatic brain injury which comprises administering to a mammal in need of such treatment a compound selected from:

(Z)-2-propenoic acid, 2-mercapto-3-[4-phenylmethoxy)phenyl];

3-(4-iodophenyl)-2-mercapto-2-propenoic acid;

(Z)-2-propenoic acid, 3-[1,1'-biphenyl]-4-yl-2-mercapto;

(Z)-2-propenoic acid, 2-mercapto-3-(9-phenanthienyl);

(Z)-2-propenoic acid, 3-2,5-dimethyl-1-phenyl-1H-pyrrol-3-yl)-2-mercapto;

(Z)-2-propenoic acid, 3-[4-(1,1-dimethylethyl)phenyl]-2-mercapto;

(Z)-2-propenoic acid, 2-mercapto-3-[4-(2-phenylethyl)phenyl];

(Z)-2-propenoic acid, 3-(3-thienyl)-2-mercapto; and (Z)-2-propenoic acid, 3-(2-[4-chlorophenyl)-1H-indol-3-yl]-2-mercapto.

17. A method for treating restenosis which comprises administering to a mammal in need of such treatment a compound selected from:

(Z)-2-propenoic acid, 2-mercapto-3-[4-(phenylmethoxy)phenyl];

3-(4-iodophenyl)-2-mercapto-2-propenoic acid, (Z)-2-propenoic acid, 3-[1,1'-biphenyl]-4-yl-2-mercapto;

(Z)-2-propenoic acid, 2-mercapto-3-(9-phenanthieyl);

(Z)-2-propenoic acid, 3-(2,5-dimethyl-1-phenyl-1H-pyrrol-3-yl)-2-mercapto;

(Z)-2-propenoic acid, 3-[4-(1,1-dimethylethyl)phenyl]-2-mercapto;

(Z)-2-propenoic acid, 2-mercapto-3-[4-(2-phenylethyl)phenyl];

(Z)-2-propenoic acid, 3-(3-thienyl)-2-mercapto; and (Z)-2-propenoic acid, 3-[2-(4-chlorophenyl)-1H-indol-3-yl]-2-mercapto.

18. A compound selected from:

3-(9-phenanthyl)-2-mercapto-2-propenoic acid;

(Z)-2-propenoic acid, 2-mercapto-3-(6-methoxy-2-naphthalenyl);

(Z)-2-propenoic acid, 3-(5-benzodioxoyl)-2-mercapto; and

2-Propenoic acid, 3-(9H-fluoren-2-yl)-2-mercapto.

* * * * *